(12) United States Patent
Doyle et al.

(10) Patent No.: US 9,017,246 B2
(45) Date of Patent: Apr. 28, 2015

(54) BILIARY CATHETER SYSTEMS INCLUDING STABILIZING MEMBERS

(75) Inventors: Eamon Doyle, La Canada, CA (US);
Clark McPheeters, Gothenburg, NE (US); David Gebhart, Richardson, TX (US); Yekaterina Miroshnikova, Hackensack, NJ (US); Lyndsey Stadtmueller, Dingman's Ferry, PA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 440 days.

(21) Appl. No.: 13/298,875

(22) Filed: Nov. 17, 2011

(65) Prior Publication Data

US 2012/0130163 A1 May 24, 2012

Related U.S. Application Data

(60) Provisional application No. 61/415,649, filed on Nov. 19, 2010.

(51) Int. Cl.
*A61B 1/00* (2006.01)
*A61B 17/00* (2006.01)
*A61B 1/313* (2006.01)
*A61B 1/018* (2006.01)
*A61B 17/32* (2006.01)
*A61B 17/22* (2006.01)
*A61B 17/30* (2006.01)
(Continued)

(52) U.S. Cl.
CPC ............ *A61B 1/313* (2013.01); *A61B 1/00087* (2013.01); *A61B 1/0011* (2013.01); *A61B 1/018* (2013.01); *A61B 17/320016* (2013.01); *A61B 2017/22074* (2013.01); *A61B 2017/306* (2013.01); *A61B 2017/3445* (2013.01); *A61B 2017/3488* (2013.01); *A61M 25/0082* (2013.01); *A61M 25/04* (2013.01)

(58) Field of Classification Search
CPC ..... A61B 1/32; A61B 17/0218; A61B 17/018
USPC .................. 600/104, 214, 210, 201, 219, 215; 606/1; 604/176
See application file for complete search history.

(56) References Cited

U.S. PATENT DOCUMENTS 2,221,138 A 11/1940 Hendrickson
2,279,297 A 4/1942 Bry
(Continued)

FOREIGN PATENT DOCUMENTS

EP 0014424 A1 8/1980
EP 0382974 A1 8/1990
(Continued)

*Primary Examiner* — Anhtuan T Nguyen
*Assistant Examiner* — Rynae Boler
(74) *Attorney, Agent, or Firm* — Seager, Tufte & Wickhem, LLC (57) ABSTRACT

Medical devices including devices and systems for endoscopic interventions that may access the biliary tree. An example biliary catheter system may include an endoscope having a working channel formed therein. An endoscopic instrument may be disposed in the channel. The endoscopic instrument may have a tool channel formed therein, a distal end, and a plurality of stabilizing members extending from the distal end. The plurality of stabilizing members may be configured to surround the ampulla of Vater during a biliary tract intervention.

20 Claims, 9 Drawing Sheets

(51) Int. Cl.
　　*A61B 17/34*　　(2006.01)
　　*A61M 25/00*　　(2006.01)
　　*A61M 25/04*　　(2006.01)

(56) References Cited

U.S. PATENT DOCUMENTS

| | | | |
|---|---|---|---|
| 2,905,178 A | 9/1959 | Hilzinger, III |
| 3,174,851 A | 3/1965 | Buchler |
| 3,338,046 A | 8/1967 | Baur Hans et al. |
| 3,351,463 A | 11/1967 | Buehler |
| 3,416,531 A | 12/1968 | Lowell |
| 3,452,742 A | 7/1969 | Muller |
| 3,453,742 A | 7/1969 | Diederen |
| 3,528,406 A | 9/1970 | Jeckel et al. |
| 3,547,103 A | 12/1970 | Cook |
| 3,552,384 A | 1/1971 | Pierie et al. |
| 3,753,700 A | 8/1973 | Harrison et al. |
| 3,757,768 A | 9/1973 | Kline |
| 3,789,841 A | 2/1974 | Antoshkiw |
| 3,890,977 A | 6/1975 | Wilson et al. |
| 3,941,119 A | 3/1976 | Corrales |
| 3,973,556 A | 8/1976 | Fleischhacker et al. |
| 4,003,369 A | 1/1977 | Heilman et al. |
| 4,020,829 A | 5/1977 | Willson et al. |
| 4,178,810 A | 12/1979 | Takahashi |
| 4,215,703 A | 8/1980 | Willson |
| 4,430,083 A | 2/1984 | Ganz et al. |
| 4,538,622 A | 9/1985 | Samson et al. |
| 4,544,929 A | 10/1985 | Lemelson |
| 4,545,390 A | 10/1985 | Leary |
| 4,554,929 A | 11/1985 | Samson et al. |
| 4,619,274 A | 10/1986 | Morrison |
| 4,665,906 A | 5/1987 | Jervis et al. |
| 4,721,117 A | 1/1988 | Mar et al. |
| 4,739,768 A | 4/1988 | Engelson |
| 4,770,188 A | 9/1988 | Chikama |
| 4,790,624 A | 12/1988 | Van Hoye et al. |
| 4,846,186 A | 7/1989 | Box et al. |
| 4,925,445 A | 5/1990 | Sakamoto et al. |
| 4,934,380 A | 6/1990 | De Toledo et al. |
| 4,966,163 A | 10/1990 | Kraus et al. |
| 4,969,890 A | 11/1990 | Sugita et al. |
| 4,971,490 A | 11/1990 | Hawkins |
| 4,984,581 A | 1/1991 | Stice |
| 4,991,602 A | 2/1991 | Amplatz et al. |
| 4,998,923 A | 3/1991 | Samson et al. |
| 5,019,040 A | 5/1991 | Itaoka et al. |
| 5,042,985 A | 8/1991 | Elliott et al. |
| 5,050,606 A | 9/1991 | Tremulis |
| 5,069,226 A | 12/1991 | Yamauchi et al. |
| 5,095,915 A | 3/1992 | Engelson et al. |
| RE33,911 E | 5/1992 | Samson |
| 5,111,829 A | 5/1992 | Alvarez de Toledo |
| 5,120,308 A | 6/1992 | Hess et al. |
| 5,129,890 A | 7/1992 | Bates et al. |
| 5,143,085 A | 9/1992 | Wilson |
| 5,144,959 A | 9/1992 | Gambale et al. |
| 5,171,383 A | 12/1992 | Sagae et al. |
| 5,213,111 A | 5/1993 | Cook et al. |
| 5,230,348 A | 7/1993 | Ishibe et al. |
| 5,238,004 A | 8/1993 | Sahatjian et al. |
| 5,267,574 A | 12/1993 | Viera et al. |
| 5,333,620 A | 8/1994 | Moutafis et al. |
| 5,341,818 A | 8/1994 | Abrams et al. |
| 5,406,960 A | 4/1995 | Corso |
| 5,409,015 A | 4/1995 | Palermo |
| 5,429,139 A | 7/1995 | Sauter |
| 5,443,907 A | 8/1995 | Slaikeu et al. |
| 5,498,250 A | 3/1996 | Prather |
| 5,772,609 A | 6/1998 | Nguyen et al. |
| 6,139,510 A | 10/2000 | Palermo et al. |
| 6,508,803 B1 | 1/2003 | Horikawa et al. |
| 6,786,898 B2 * | 9/2004 | Guenst ............... 606/1 |
| 2005/0113683 A1 | 5/2005 | Lokhandwalla et al. |
| 2007/0038042 A1 | 2/2007 | Freeman et al. |
| 2007/0168016 A1 | 7/2007 | Gronemeyer et al. |
| 2008/0015416 A1 * | 1/2008 | Rucker ............... 600/210 |
| 2008/0167691 A1 | 7/2008 | Weintraub |
| 2008/0262301 A1 * | 10/2008 | Gibbons et al. ...... 600/114 |
| 2008/0312550 A1 | 12/2008 | Nishtala et al. |
| 2008/0319339 A1 | 12/2008 | Beute |
| 2009/0131755 A1 | 5/2009 | White et al. |
| 2009/0137878 A1 * | 5/2009 | Rivera et al. ........ 600/206 |
| 2009/0312645 A1 | 12/2009 | Weitzner et al. |
| 2010/0010299 A1 | 1/2010 | Bakos et al. |
| 2010/0016662 A1 | 1/2010 | Salsman et al. |
| 2010/0022845 A1 | 1/2010 | Ott et al. |
| 2010/0030109 A1 | 2/2010 | Lin |

FOREIGN PATENT DOCUMENTS

| | | |
|---|---|---|
| EP | 0491349 A2 | 6/1992 |
| EP | 0515201 A1 | 11/1992 |
| EP | 0519604 A2 | 12/1992 |
| WO | 9115152 A1 | 10/1991 |
| WO | 9214506 A1 | 9/1992 |

* cited by examiner

BILIARY CATHETER SYSTEMS INCLUDING STABILIZING MEMBERS

CROSS REFERENCE TO RELATED APPLICATIONS

This application claims the benefit of U.S. Provisional Application Ser. No. 61/415,649, filed Nov. 19, 2010, the disclosure of which is incorporated herein in its entirety.

TECHNICAL FIELD

The present invention pertains to medical devices, and methods for manufacturing medical devices. More particularly, the present invention pertains to biliary catheter systems and instruments and/or tools that are designed to provide enhanced stabilization during a biliary tree intervention.

BACKGROUND

A wide variety of medical devices have been developed for medical use, for example, endoscopic use. Some of these devices include catheters, catheter systems, endoscopic instruments, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices such as catheters, catheter systems, endoscopic instruments, biliary catheters and catheter systems, tools including stabilizing tools, and the like. An example biliary catheter system may include an endoscope having a working channel formed therein. An endoscopic instrument may be disposed in the channel. The endoscopic instrument may have a tool channel formed therein, a distal end, and a plurality of stabilizing members extending from the distal end. The plurality of stabilizing members may be configured to surround the ampulla of Vater during a biliary tract intervention.

An example stabilization tool for cannulation of an ampulla of Vater of a patient may include an endoscopic instrument configured to be disposed in a channel of an endoscope. The endoscopic instrument may have a cannulation tool channel formed therein, a distal end, and three or more stabilizing members extending from the distal end for stabilizing the endoscopic instrument relative to the ampulla of Vater during a biliary tract intervention. The stabilizing members may be arranged so as to surround the ampulla of Vater during the intervention. A cannulation tool may be disposed in the cannulation tool channel.

An example method for cannulation of an ampulla of Vater of a patient may include providing an endoscope having a channel formed therein, advancing the endoscope to a position adjacent to the ampulla of Vater and advancing a stabilization and cannulation tool through the channel of the endoscope. The tool may include an endoscopic instrument having a cannulation tool channel formed therein, a distal end, and three or more stabilizing members extending from the distal end. The tool may also include a cannulation tool disposed in the cannulation tool channel. The method may also include arranging the endoscopic instrument so that the stabilizing members surround and stabilize the ampulla of Vater and delivering the cannulation tool to the ampulla of Vater.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Endoscopic retrograde cholangiopancreatography (ERCP) is used primarily to diagnose and treat conditions of the bile ducts including, for example, gallstones, inflammatory strictures, leaks (e.g., from trauma, surgery, etc.), and cancer. Through the endoscope, the physician can see the inside of the stomach and duodenum, and inject dyes into the ducts in the biliary tree and pancreas so they can be seen on x-rays. These procedures may necessitate gaining and keeping access to the biliary duct, which may be technically challenging, may require extensive training and practice to gain proficiency, and may require one or more expensive tools in order to perform.

During an ERCP procedure, a number of steps are typically performed while the patient is often sedated or anaesthetized. For example, an endoscope may be inserted through the mouth, down the esophagus, into the stomach, through the pylorus into the duodenum, to a position at or near the ampulla of Vater (the opening of the common bile duct and pancreatic duct). Due to the shape of the ampulla and the angle at which the common bile and pancreatic ducts meet the wall of the duodenum, the distal end of the endoscope is generally placed just past the ampulla. Due to the positioning of the endoscope beyond the ampulla, the endoscopes used in these procedures are usually side-viewing endoscopes. The side-viewing feature provides imaging along the lateral aspect of the tip rather than from the end of the endoscope. This allows the clinician to obtain an image of the medial wall of the duodenum, where the ampulla of Vater is located, even though the distal tip of the endoscope is beyond the opening.

Next, a clinician may cannulate the entrance to the pancreatic and bile ducts, which are located beyond the ampulla of Vater, with a catheter or cannula placed through the instrument channel of the endoscope. The catheters are directed cranially at an angle with respect to the distal end of the endoscope, so as to facilitate insertion into the opening. Once in place within the ampulla, a radiocontrast agent can be injected into the bile ducts and/or pancreatic duct. Fluoroscopy can then be used to identify and treat various ailments, including blockages or leakage of bile into the peritoneum (abdominal cavity).

Because the ampulla of Vater is positioned within the duodenum, and because the duodenum may be moving due to peristalsis, positioning and cannulating the ampulla of Vater may be challenging. Disclosed herein are systems, tools, and methods for cannulating the ampulla of Vater during the diagnosis and treatment of biliary, hepatic, gallbladder, and/or pancreatic disease or other ailments. The systems, tools, and methods disclosed are generally directed at improving the ability of a user to cannulate the ampulla of Vater by helping to stabilize a portion of the duodenum near the ampulla during the cannulization procedure.

Figure 1:
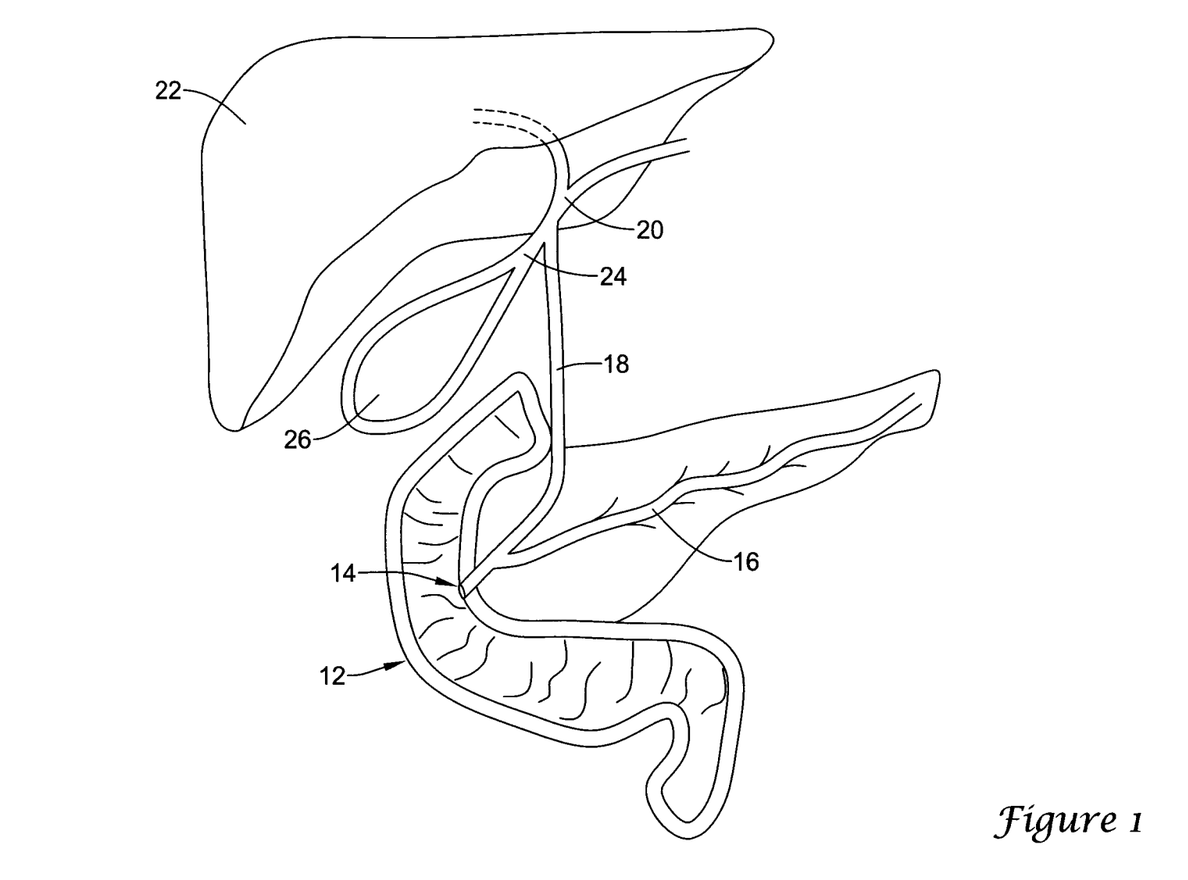
FIG. 1 is an overview of the biliary tree.

FIG. 1 provides an overview of the biliary system or tree. Illustrated is a portion of the duodenum 12 where the ampulla of Vater 14 is located. For the purposes of this disclosure, the ampulla of Vater 14 is understood to be the same anatomical structure as the papilla of Vater. The ampulla of Vater 14 generally forms the opening where the pancreatic duct 16 and the bile duct 18 can empty into the duodenum 12. The hepatic ducts, generally bearing reference number 20, are connected to the liver 22 and empty into the bile duct 18. Likewise, the cystic duct 24, which is connected to the gall bladder 26, also empties into the bile duct 18. In general, an endoscopic or biliary procedure may include advancing a medical device to a suitable location along the biliary tree and then performing the appropriate intervention.

Figure 2:
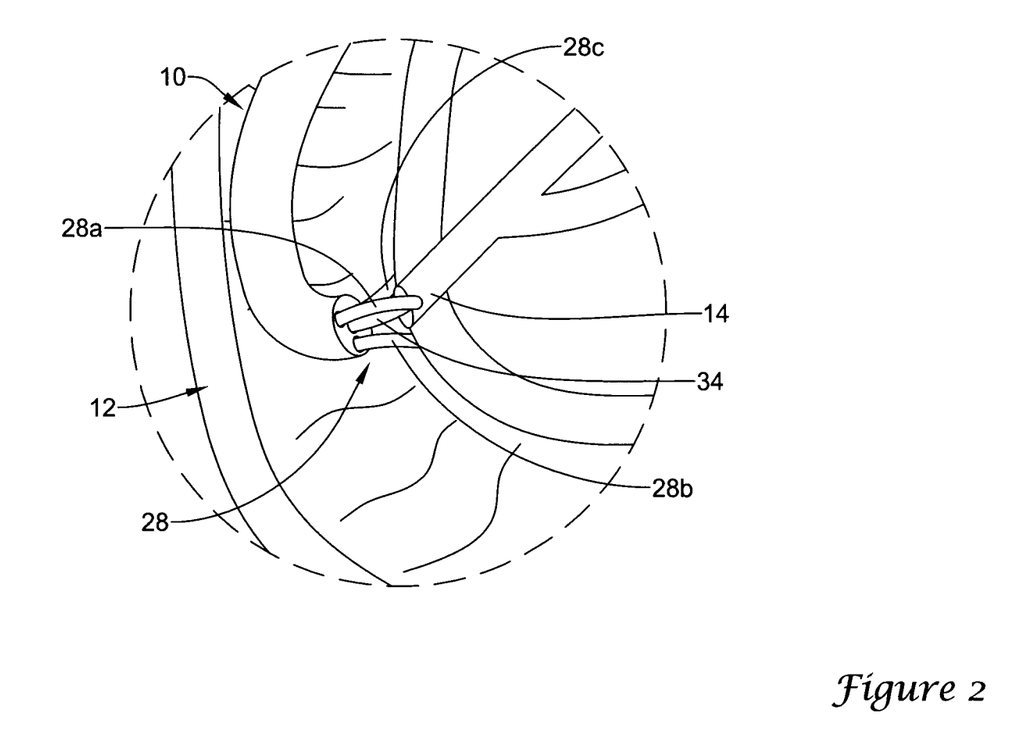
FIG. 2 is a plan view illustrating an example endoscope system disposed adjacent to the ampulla of Vater.

FIG. 2 illustrates a distal portion of an endoscope system 10 that has advanced through the mouth of a patient, through the stomach, and into the duodenum 12 adjacent the ampulla of Vater 14. In order to gain access the biliary tree, system 10 and/or a catheter or cannulation tool will "cannulate" or otherwise pass through the ampulla of Vater 14. However, due to peristalsis the duodenum 12 adjacent the ampulla of Vater 14 may be moving, which may make it technically difficult to cannulate the ampulla of Vater 14. In order to more efficiently cannulate the ampulla of Vater 14, system 10 may include a stabilizing assembly 28 that functions by "stabilizing" or otherwise helping reduce the peristaltic motion of the duodenum 12 so that a clinician can cannulate the ampulla of Vater 14 in a relatively simple and time-efficient manner.

In at least some embodiments, stabilizing assembly 28 includes a plurality of stabilizing members including a first stabilizing member 28a, a second stabilizing member 28b, and a third stabilizing member 28c. In use, stabilizing members 28a/28b/28c can be disposed about the ampulla of Vater 14. This may include positioning stabilizing members 28a/28b/28c so they surround or otherwise are disposed along multiple points of the periphery of the ampulla of Vater 14. Such positioning may be desirable for a number of reasons. For example, positioning stabilizing members 28a/28b/28c so that they surround the ampulla of Vater 14 may allow stabilizing assembly 28 to sufficiently stabilize the duodenum 12, which may be moving due to peristalsis, so that a cannulation tool 34 can cannulate the ampulla of Vater 14. In addition, because stabilizing members 28a/28b/28c may be disposed along "all sides" of the ampulla of Vater 14, the ampulla of Vater 14 may be more fully stabilized than if system 10 was just secured to one or two points along the wall of the duodenum 12.

Figure 3:
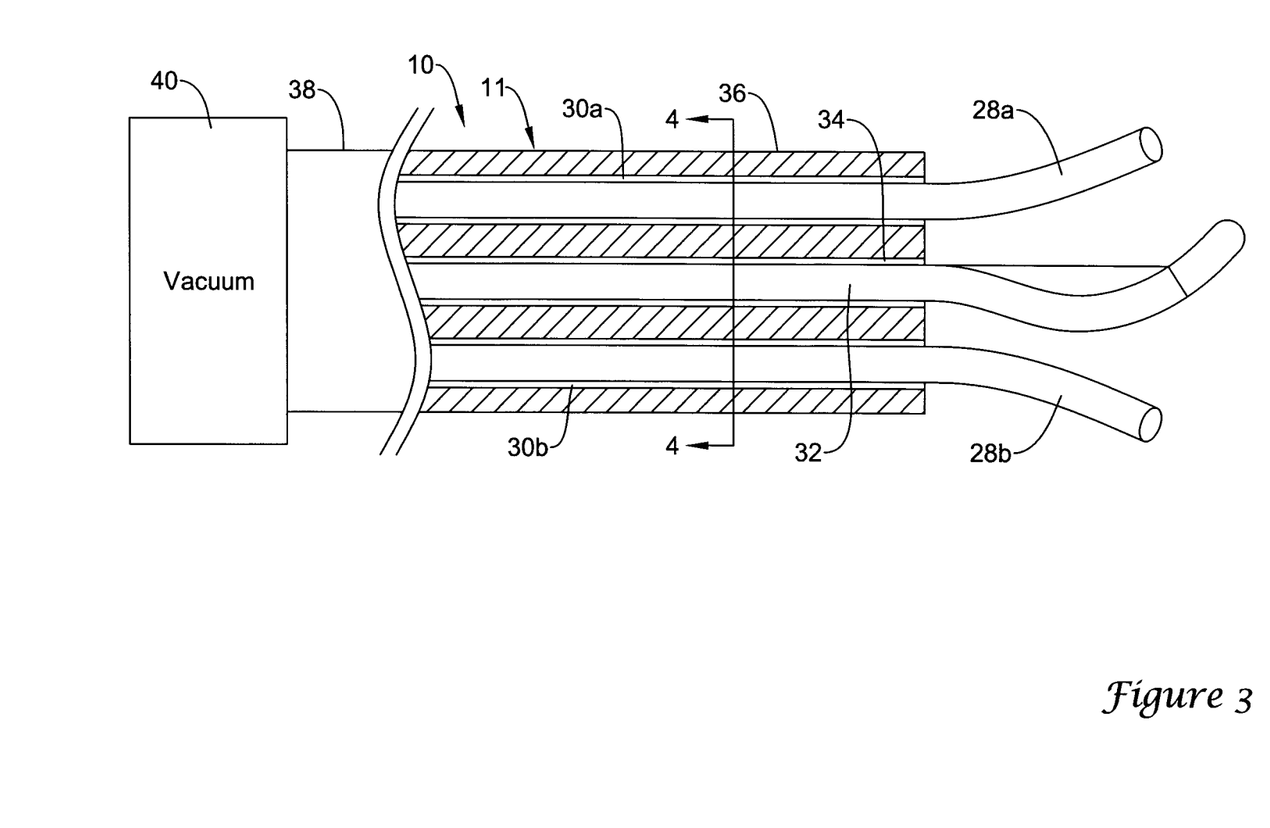
FIG. 3 is a partial cross-sectional side view of an example tubular member including a plurality of stabilizing members.

FIG. 3 is a partial cross-section side view of system 10 and provides some additional details regarding system 10. Here it can be seen that system 10 may include a tubular member 11. In some embodiments, tubular member 11 is a portion of an endoscope or is the shaft of an endoscope. In other embodiments, tubular member 11 is an endoscopic instrument or tool that is configured to be disposed in a channel or lumen formed in an endoscope. According to this later embodiment, tubular member 11 may be configured to be advanced through a channel formed in an endoscope and extend out from a port at or near the distal end (e.g., including a side port formed along a side surface) of the endoscope.

Figure 4:
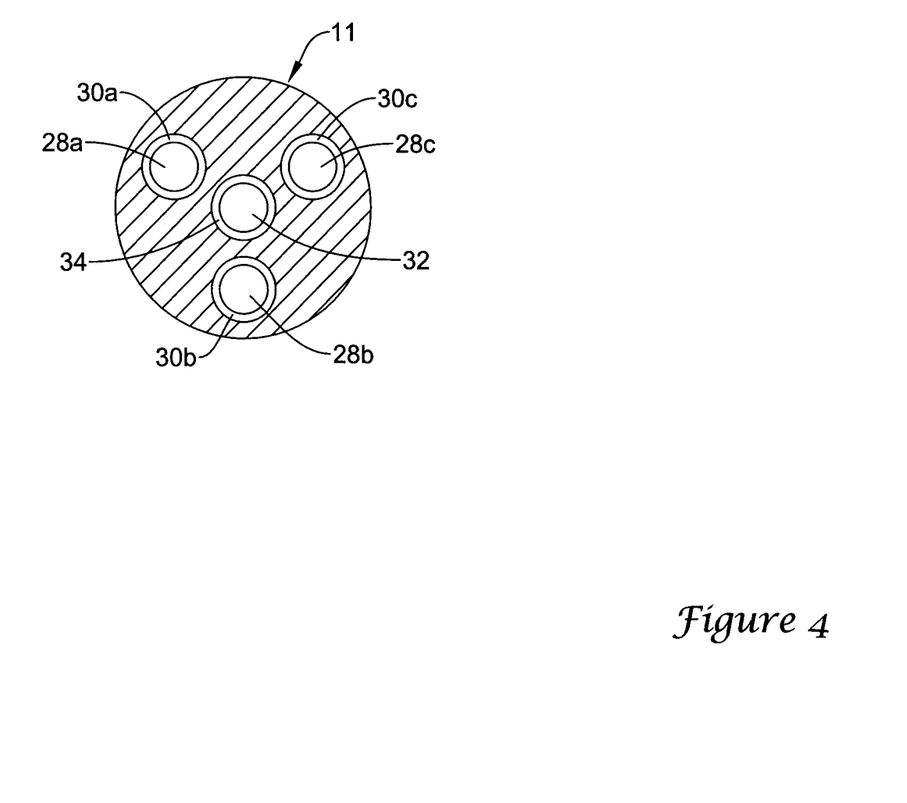
FIG. 4 is a partial transverse cross-sectional view of the example tubular member illustrated in FIG. 3.

Tubular member 11 may have a plurality of lumens or channels formed therein. For example, a first lumen 30a and a second lumen 30b may be formed in tubular member 11. A third lumen 30c may also be formed in tubular member 11 as more clearly seen in FIG. 4. Stabilizing assembly 28 may be disposed within tubular member 11. For example, first stabilizing member 28a may be disposed in first lumen 30a, second stabilizing member 28b may be disposed in second lumen 30b, and third stabilizing member 28c may be disposed in third lumen 30c as shown in FIG. 4.

The precise structural arrangement of stabilizing assembly 28 relative to tubular member 11 may vary. For example, in the embodiment illustrated in FIGS. 2-4, the various stabilizing members 28a/28b/28c of stabilizing assembly 28 are separately disposed in lumens 30a/30b/30c of tubular member 11, respectively. At a proximal portion 38 of tubular member 11, stabilizing members 28a/28b/28c may be secured to an actuation or advancing mechanism (not shown) that allows stabilizing members 28a/28b/28c to be advanced out from and be retracted back into a distal portion 36 of tubular member. The actuation mechanism may be an integrated structure that allows all three of stabilizing members 28a/28b/28c to be advanced or retracted together. Alternatively, the proximal ends of stabilizing members 28a/28b/28c may be accessible to the clinician so that each can be independently advanced and/or retracted to the extent desired so as to best perform the intended intervention. Numerous other arrangements, configurations, and/or actuation mechanisms are contemplated.

In order to assist with stabilizing the duodenum 12, stabilizing members 28a/28b/28c may comprise vacuum lumens that are configured to extend out from the distal portion 36 of tubular member 11 and engage the wall of the duodenum 12. Once engaged, a vacuum can be applied to stabilizing members 28a/28b/28c (e.g., to vacuum channels defined by generally tubular stabilizing members 28a/28b/28c and/or through lumens 30a/30b/30c), via a vacuum source 40 coupled to the proximal portion 38 of tubular member 11, so that stabilizing members 28a/28b/28c can adhere to and hold on to the wall of the duodenum 12. Because stabilizing members 28a/28b/28c surround or are otherwise disposed at multiple positions along the periphery of the ampulla of Vater 14, stabilizing members 28a/28b/28c can reduce the peristaltic motion of the duodenum 12 adjacent the ampulla of Vater 14 so that a clinician can cannulate the ampulla of Vater 14 in an efficient manner.

In at least some embodiments, stabilizing members 28a/28b/28c may be biased to project somewhat radially outward when extending out from distal portion 36 of tubular member 11. This may be desirable, for example, because it may create a "fan-like" or funnel-shaped orientation of stabilizing members 28a/28b/28c. The shape of this configuration may also be described as being triangular. Because of this, stabilizing members 28a/28b/28c may more easily surround the ampulla of Vater 14. In some embodiments, stabilizing members 28a/28b/28c may be biased by simply being arranged in a slightly bent or bowed configuration prior to being disposed in lumens 30a/30b/30c such that extending stabilizing members 28a/28b/28c out from distal portion 36 allows stabilizing members 28a/28b/28c to resume their bent configuration. Alternatively, one or more biasing springs or levers may be disposed adjacent distal portion 36 that exert a radially outward force on stabilizing members 28a/28b/28c so as to help stabilizing members 28a/28b/28c take the desired configuration. In some embodiments, the angle or bend at which stabilizing members 28a/28b/28c are oriented can be adjusted. This may include the use of pull wires (not shown, which may extend down lumens 30a/30b/30c) or any other suitable bending mechanism. Numerous other configurations are contemplated for orienting or adjusting the shape configuration of stabilizing members 28a/28b/28c including, for example, guides formed at distal portion 36 that may function analogously to the guides described below and shown in FIG. 7.

Cannulation may occur through the use of a cannulation tool 32 that may extend through a cannulation tool lumen 34 formed in tubular member 11. The form of cannulation tool 32 may vary widely. In some embodiments, cannulation tool 32 may be a catheter, a stent (e.g., a biliary or "drainage" stent) delivery system, tomes or cutting devices, balloon devices, ERCP devices, needle devices, knife devices, or the like. For example, in FIG. 3, cannulation tool 32 is illustrated as a sphincterotome that may be utilized to help cannulate the ampulla of Vater 14 and/or other portions of the biliary tree. In general, cannulation tool 32 is brought to the area of interest by placing tool 32 adjacent to stabilizing assembly 28. This may include passing tool 32 through lumen 34 or otherwise disposing tool 34 near stabilizing assembly.

While FIGS. 2-4 illustrate stabilizing assembly 28 as having three stabilizing members 28a/28b/28c taking the form of vacuum lumens, this is not intended to be limiting as the precise number and form of stabilizing assembly 28 may vary. For example, stabilizing assembly 28 may include any suitable number of stabilizing members including one, two, three, four, five, six, seven, eight, nine, ten, or more. These stabilizing members may all have essentially the same structure or form or they may vary from one another. For example, some stabilizing members may take the form of vacuum lumens whereas others may have another form that may desirably aid in stabilizing the wall of the duodenum 12. Some examples of other types of stabilizing members are disclosed herein. Numerous other stabilizing members and/or combinations of stabilizing members are contemplated.

It can be appreciated that the shape or pattern formed by stabilizing assembly 28 or other stabilizing assemblies disclosed or contemplated herein may vary depending on the number of stabilizing members utilized and, for example, the shape that may best be suited for surrounding the ampulla of Vater 14. For example, stabilizing assembly 28 may have a generally triangular shape when disposed about the ampulla of Vater 14. Other shapes, however, are contemplated particularly when a different numbers of stabilizing members are utilized in stabilizing assembly 28. For example, four stabilizing members may take the form of a square or rectangular shape. Other shapes are contemplated such as a pentagon, a hexagon, a heptagon, an octagon, a nonagon, a decagon, a generally circular shape, a generally oval shape, a star shape, a pill shape, etc.

In addition, each of the stabilizing members may extend through an individual (e.g., its own) lumen formed in tubular member 11 as shown in FIGS. 2-4 or one or more stabilizing members may share a common lumen. Some embodiments may include some stabilizing members that extend through their own individual lumens and some other stabilizing members that share a common lumen in one stabilizing assembly. Numerous other arrangements or differences in form are also contemplated.

Figure 4A:
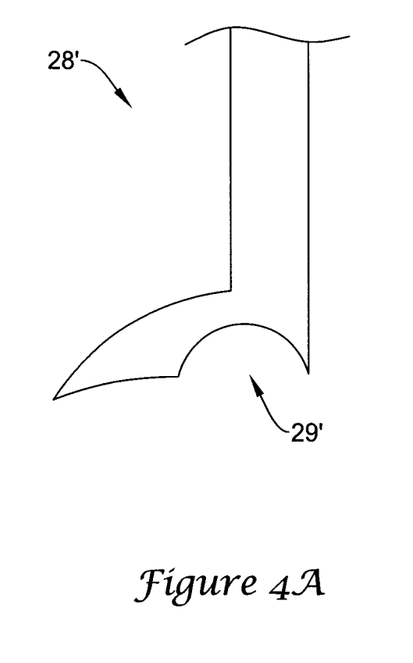
FIG. 4A is a plan view of a portion of an example stabilizing member.
Figure 4B:
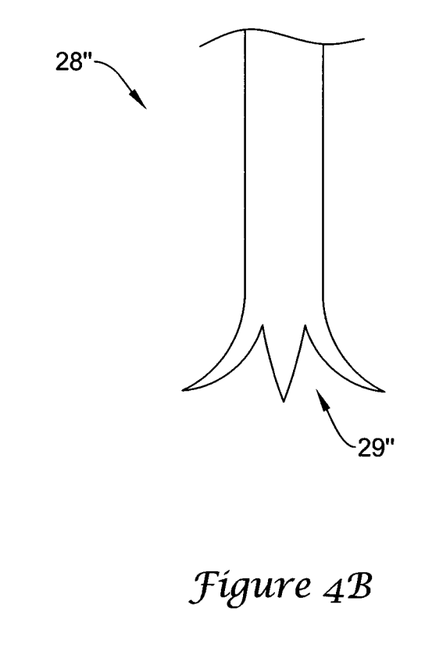
FIG. 4B is a plan view of a portion of another example stabilizing member.

In addition, one or more of the stabilizing members may include other structural features that help to further enhance stabilization. For example, FIG. 4A illustrates a stabilizing member bearing reference number 28', which has a curved or bend contact area 29'. Area 29' may correspond to the surface of stabilizing member 28' that contacts the target anatomy, for example along the periphery of the ampulla of Vater 14. Area 29' may increase the contact area between stabilizing member 28' and the target anatomy. In addition, other stabilizing member are contemplated such as stabilizing member 28", illustrated in FIG. 4B, which includes a plurality of projections or "toes" 29" along its end. Toes 29" may also increase the contact area between stabilizing member 28" and the target anatomy. The features of stabilizing members 28'/28" may be included in any of the stabilizing members disclosed herein. Additionally, other stabilizing members are also contemplated that may include other structural similar to those of stabilizing members 28'/28" such as, for example, a webbed and/or a fanned structure (not shown), which may be configured to expand so as to increase the contact area between the stabilizing member and the target anatomy, for example along the periphery of the ampulla of Vater 14.

Figure 5:
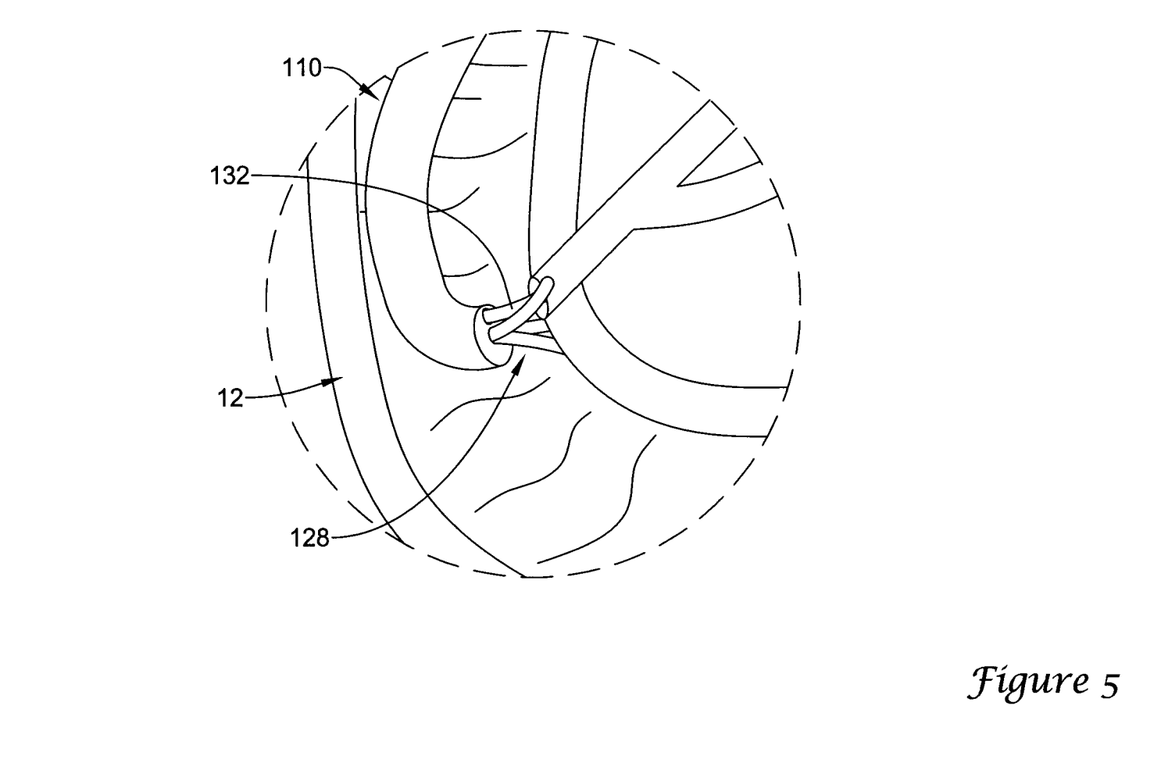
FIG. 5 is a plan view illustrating another example endoscope system disposed adjacent to the ampulla of Vater.
Figure 6:
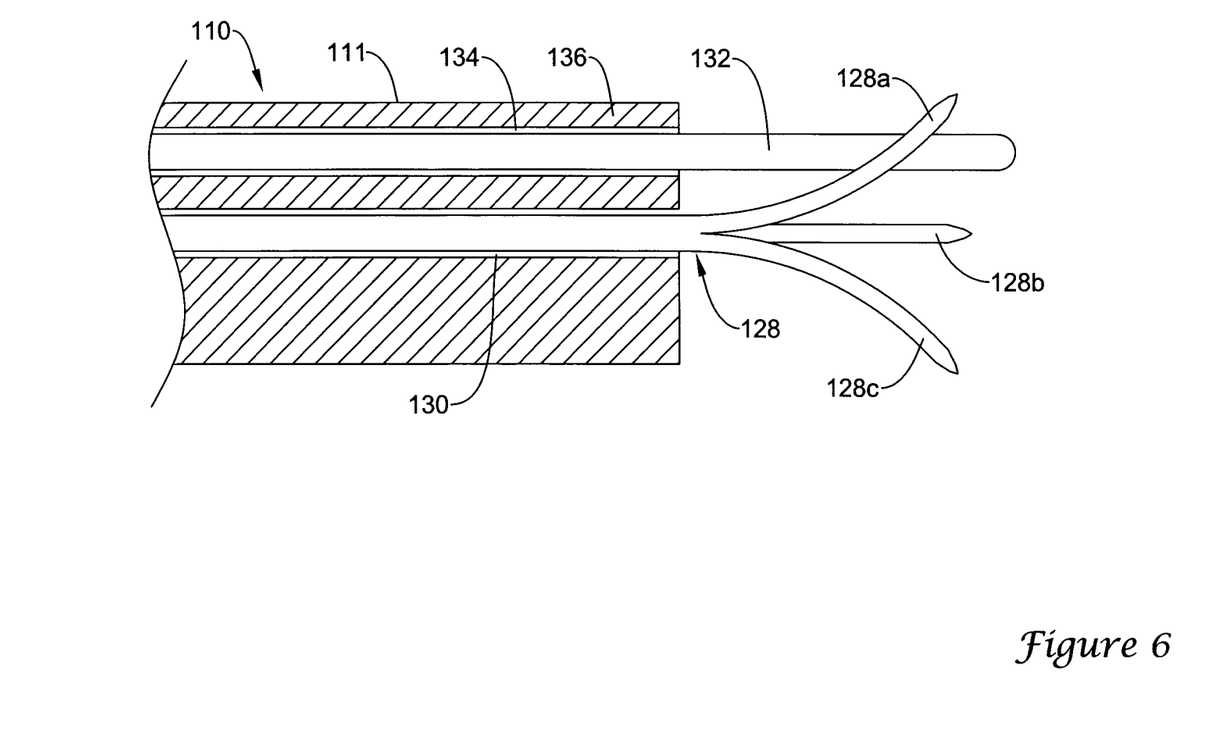
FIG. 6 is a partial cross-sectional side view of another example tubular member including a plurality of stabilizing members.
Figure 7:
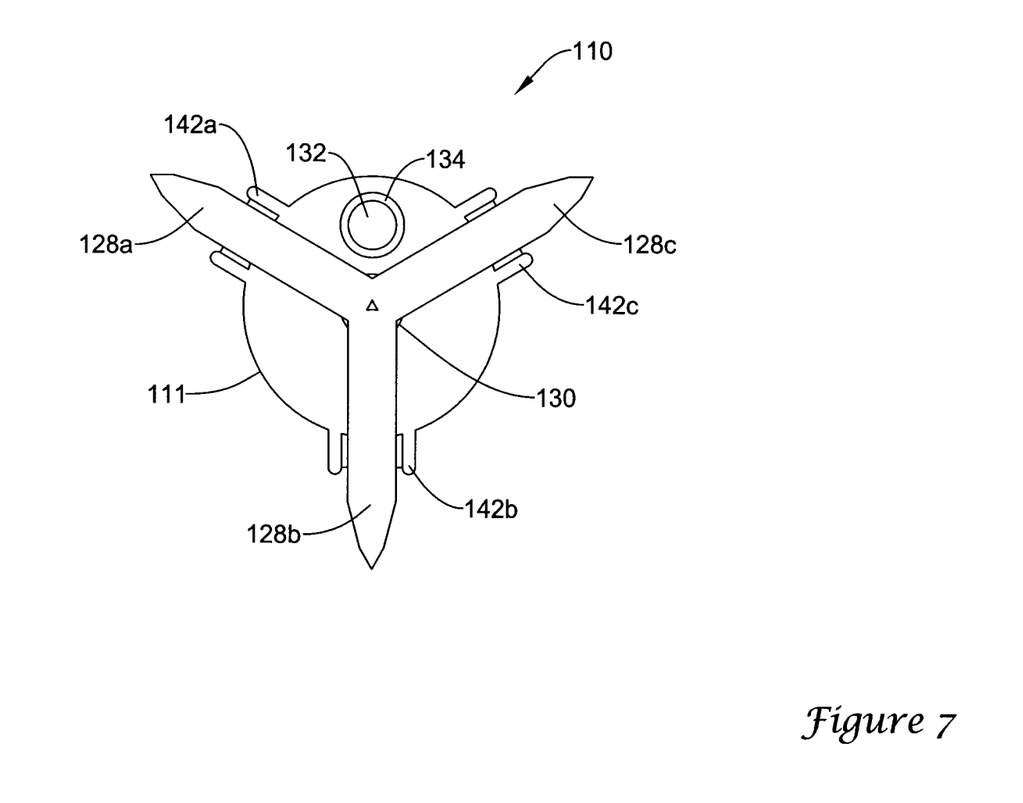
FIG. 7 is an end view of the example tubular member illustrated in FIG. 6.

FIGS. 5-7 illustrate another endoscope system 110, which may be similar in form and function to system 10. System 110 may include stabilizing assembly 128, which may include three stabilizing legs 128a/128b/128c that are configured to extend out from tubular member 111 and surround or otherwise be disposed at multiple positions along the periphery of the ampulla of Vater 14 in order to stabilize the ampulla of Vater 14. In the illustrated embodiment, for example as shown in FIG. 6, stabilizing legs 128a/128b/128c may be disposed in lumen 130. Lumen 130 may be a single, common lumen 130 through which all of stabilizing legs 128a/128b/128c may extend. However, this is not intended to be limiting as other embodiments are contemplated where each individual stabilizing lever 128a/128b/128c extends through its own lumen formed in tubular member 111.

Stabilizing members 128a/128b/128c may have a sharpened or otherwise pointed end that may allow stabilizing members 128a/128b/128c to engage and secure with duodenum 12. It can be appreciated that these pointed ends have points of a suitable size so as to effectively engage duodenum 12 while minimizing any potential damage to the wall of the duodenum 12. In other embodiments, stabilizing members 128a/128b/128c may be roughened or otherwise altered so that they can frictionally engage duodenum 12 and, thus, secure stabilizing assembly 128 to the wall of the duodenum 12.

Stabilizing members 128a/128b/128c can be advanced out from distal portion 136 of tubular member 111 so as to be brought into contact with the duodenum 12. When in contact with the duodenum 12, cannulation tool 132, which may be similar in form and function to other tools disclosed herein, may extend through lumen 134 and cannulate the ampulla of Vater 14.

Just like in stabilizing assembly 28, stabilizing legs 128a/128b/128c may be biased to expand radially outward when advanced out of distal portion 136 of tubular member 111. This may be due to the material or shape of stabilizing legs 128a/128b/128c (e.g., stabilizing legs 128a/128b/128c may have a bent configuration when not disposed in lumen 130), due to a spring or a biasing structure, or due to any other suitable structural arrangement.

FIG. 7 is an end view of system 110. Here it can be seen that tubular member 111 may include a plurality of guides such as a first guide 142a, a second guide 142b, a third guide 142c that help guide stabilizing legs 128a/128b/128c to the desired configuration about the ampulla of Vater 14. Guides 142a/142b/142c may serve as a structure that help orient stabilizing legs 128a/128b/128c in the desired configuration, which in this case may be a generally triangular shape that can essentially surround the ampulla of Vater 14. To orient stabilizing legs 128a/128b/128c, guides 142a/142b/142c may form a structural barrier that may limit the radial expansion of stabilizing legs 128a/128b/128c so that stabilizing legs 128a/128b/128c can form a substantially "tight" triangular orientation about the ampulla of Vater 14. It can be appreciated that guides 142a/142b/142c can be arranged so that stabilizing legs 128a/128b/128c expand to the degree desired and in some embodiments, guides 142a/142b/142c may be adjustable by the clinician (either before or during an intervention) so that the extent of radial expansion can be altered to best suit the needs of a given intervention.

Figure 8:
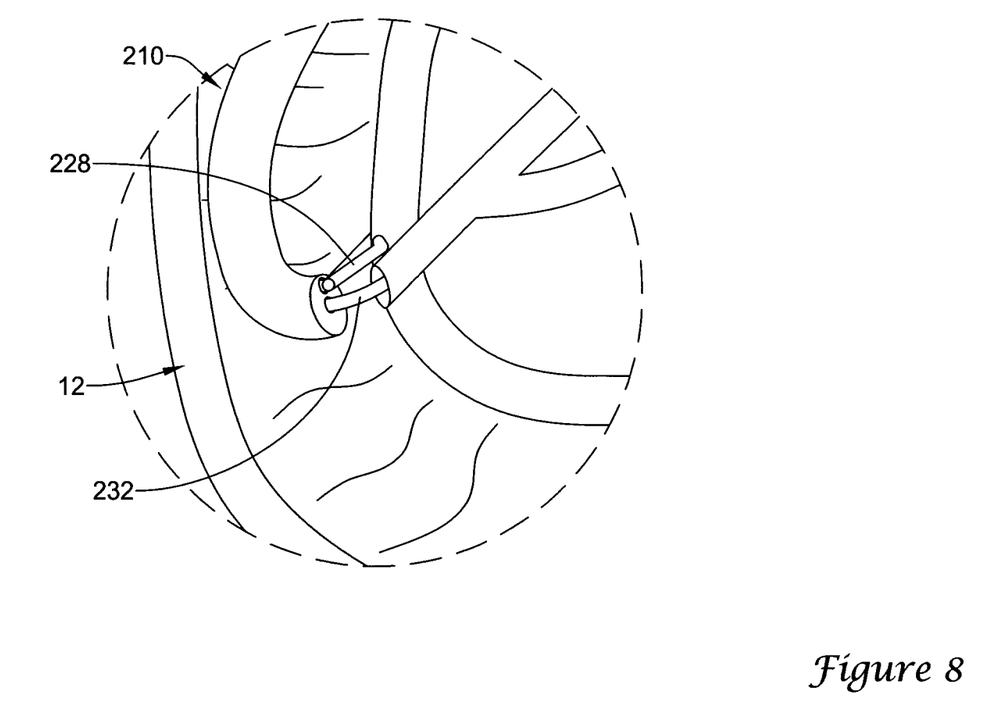
FIG. 8 is a plan view illustrating another example endoscope system disposed adjacent to the ampulla of Vater.

Another endoscope system 210 is illustrated in FIG. 8. System 210 may include a stabilizing clip 228 that can extend from system 210 so that cannulation tool 232 can cannulate the ampulla of Vater 14. Clip 228 may generally be configured to engage a portion of the wall of the duodenum 12 and secure it with the jaws of the clip 228. Clip 228 may be actuated by a control member or wire (not shown) that may extend within system 210 and be accessible to the clinician.

While system 210 is illustrated as having only a singular stabilizing structure (e.g., stabilizing clip 228), it is contemplated that clip 228 may be used in combination with and/or form part of any of the other stabilizing assembly disclosed herein. For example, stabilizing assembly 28 and/or stabilizing assembly 128 may include clip 228. In such embodiments, clip 228 may share one of the lumens of the respective tubular member 11/111 or it may be disposed in a separate lumen formed in the respective tubular member 11/111.

The materials that can be used for the various components of system 10 (and/or other systems disclosed herein) may include those commonly associated with medical devices. For simplicity purposes, the following discussion makes reference to system 10, tubular member 11, and stabilizing assembly 28. However, this is not intended to limit the invention as the discussion may be applied to other similar members and/or components of members or systems disclosed herein.

Tubular member 11, stabilizing assembly 28, and/or other components of system 10 may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of tubular member 11 and/or stabilizing assembly 28 may also be doped with, made of, or otherwise include a radiopaque material including those listed herein or other suitable radiopaque materials. In some embodiments, a degree of MRI compatibility is imparted into system 10.

For example, to enhance compatibility with Magnetic Resonance Imaging (MRI) machines, it may be desirable to make tubular member 11 and/or stabilizing assembly 28 in a manner that would impart a degree of MRI compatibility. For example, tubular member 11, stabilizing assembly 28, or portions thereof, may be made of a material that does not substantially distort the image and create substantial artifacts (artifacts are gaps in the image). Certain ferromagnetic materials, for example, may not be suitable because they may create artifacts in an MRI image. Tubular member 11, stabilizing assembly 28, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be used to form tubular member 11, stabilizing assembly 28, and/or other components of system 10 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In some embodiments, the exterior surface of the system 10 may include a coating, for example a lubricious, a hydrophilic, a protective, or other type of coating. Hydrophobic coatings such as fluoropolymers provide a dry lubricity which improves device handling and exchanges. Lubricious coatings improve steerability and improve lesion crossing capability. Suitable lubricious polymers may include silicone and the like, polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, the entire disclosures of which are incorporated herein by reference. Other coatings may be utilized, as desired, to increase surface friction or otherwise add a tacky or adhesive-like (e.g., sticky) feel.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A biliary catheter system, comprising:
   an endoscope having a working channel formed therein; and
   an endoscopic instrument disposed in the working channel, the endoscopic instrument having a tool channel formed therein, a distal end, and a plurality of stabilizing members each extending through the endoscopic instrument and extending from the distal end, wherein the plurality of stabilizing members are configured to surround the ampulla of Vater during an endoscopic intervention;

wherein a proximal end of each of the plurality of stabilizing members is accessible for independent manipulation of each stabilizing member.

2. The system of claim 1, further comprising a cannulation tool disposed in the tool channel.

3. The system of claim 1, wherein the stabilizing members comprise vacuum lumens.

4. The system of claim 3, further comprising a vacuum source coupled to the vacuum lumens.

5. The system of claim 1, wherein the endoscopic instrument includes three or more stabilizing members.

6. The system of claim 1, wherein the stabilizing members include stabilizing legs.

7. The system of claim 6, wherein each of the stabilizing legs have a point formed thereon.

8. The system of claim 1, wherein the stabilizing members include a clip.

9. The system of claim 1, wherein the endoscopic instrument includes three stabilizing members, wherein the stabilizing members each have a distal end, and wherein the distal ends are arranged in a substantially triangular configuration when deployed.

10. The system of claim 1, wherein the endoscopic instrument has a single stabilizing member channel formed therein, and wherein all of the stabilizing members extend through the single stabilizing member channel.

11. The system of claim 1, wherein the endoscopic instrument includes a plurality of stabilizing member channels formed therein, and wherein each of stabilizing members is disposed in one of the stabilizing member channels.

12. A stabilization tool for cannulation of an ampulla of Vater of a patient, the system comprising:

an endoscopic instrument configured to be disposed in a channel of an endoscope, the endoscopic instrument having a cannulation tool channel formed therein, a proximal end, a distal end, and a stabilizing assembly extending axially through the endoscopic instrument, the stabilizing assembly including three or more stabilizing members all extending from the proximal end to the distal end and extending from within the distal end for stabilizing the endoscopic instrument relative to the ampulla of Vater during a biliary tract intervention;

wherein the stabilizing members are arranged so as to surround the ampulla of Vater during the intervention; and a cannulation tool disposed in the cannulation tool channel.

13. The tool of claim 12, wherein the stabilizing members comprise vacuum lumens.

14. The tool of claim 12, wherein the stabilizing members include three or more stabilizing legs that each have a point formed thereon.

15. The tool of claim 12, wherein the stabilizing members include a clip.

16. The tool of claim 12, wherein the stabilizing members each have a distal end, and wherein the distal ends are arranged in a substantially triangular configuration when deployed.

17. The tool of claim 12, wherein the endoscopic instrument has a stabilizing member channel formed therein, and wherein all of the stabilizing members extend through the stabilizing member channel.

18. The tool of claim 12, wherein the endoscopic instrument includes a plurality of stabilizing member channels formed therein, and wherein each of stabilizing members is disposed in one of the stabilizing member channels.

19. A method for cannulation of an ampulla of Vater of a patient, the method comprising:

providing an endoscope having a channel formed therein;

advancing the endoscope to a position adjacent to the ampulla of Vater;

advancing a stabilization and cannulation tool through the channel of the endoscope, the tool comprising:

an endoscopic instrument having a cannulation tool channel formed therein, a distal end, and a stabilizing assembly including three or more stabilizing members disposed within the endoscopic instrument, and a cannulation tool disposed in the cannulation tool channel;

extending distal ends of the three or more stabilizing members from the distal end of the endoscopic instrument so that the stabilizing members surround and stabilize the ampulla of Vater relative to the endoscopic instrument, while maintaining proximal ends of the three or more stabilizing members within the endoscopic instrument; and delivering the cannulation tool to the ampulla of Vater.

20. The method of claim 19, wherein the stabilizing members include one or more of a vacuum lumen, a lever having a point formed thereon, and a clip.

* * * * *